US00PP24392P3

(12) United States Plant Patent
Korlipara

(10) Patent No.: US PP24,392 P3
(45) Date of Patent: Apr. 15, 2014

(54) *ECHINACEA* PLANT NAMED 'ROSITA'

(50) Latin Name: ***Echinacea* hybrid**
Varietal Denomination: Rosita

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 65 days.

(21) Appl. No.: 13/573,344

(22) Filed: Sep. 11, 2012

(65) Prior Publication Data

US 2014/0075634 P1 Mar. 13, 2014

(51) Int. Cl.
*A01H 5/00* (2006.01)

(52) U.S. Cl.
CPC ..... *A01H 5/00* (2013.01)
USPC ..... Plt./428

(58) Field of Classification Search
CPC ..... A01H 4/00; A01H 5/00; A01H 1/04; A01H 1/06
USPC ..... Plt./428
See application file for complete search history.

*Primary Examiner* — Annette Para
(74) *Attorney, Agent, or Firm* — Klarquist Sparkman, LLP

(57) ABSTRACT

A new and distinct *Echinacea* plant named 'Rosita' characterized by light pink ray florets, numerous, medium to small size inflorescences, a well branched, compact, dwarf habit, and excellent vigor.

1 Drawing Sheet

Botanical denomination: *Echinacea* hybrid.
Variety designation: 'Rosita'.

BACKGROUND OF THE INVENTION

The present invention relates to a new and distinct cultivar of *Echinacea* and given the cultivar name 'Rosita'. *Echinacea* is in the family Asteraceae. This new cultivar is part of a planned breeding program to develop dwarf *Echinacea* hybrids. This cultivar was selected for its compact free flowering habit with light pink inflorescences. The exact parents of this selection are unknown, unnamed, proprietary interspecific hybrid plants.

Compared to *Echinacea* 'Little Angel' (U.S. Plant Pat. No. 21,870), the new cultivar has light pink ray florets rather than white.

Compared to *Echinacea* 'Kim's Knee Hi', an unpatented plant, the new cultivar has lighter pink ray florets and is much shorter.

This new *Echinacea* cultivar is distinguished by:

1. light pink ray florets,
2. numerous, medium to small size inflorescences,
3. a well branched, compact, dwarf habit, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the inflorescences of *Echinacea* 'Rosita' on a one-year-old plant growing in the field in full sun in early July in Canby, Oreg.

DETAILED PLANT DESCRIPTION

The following is a detailed description of the new *Echinacea* cultivar based on observations of a two-year-old specimen growing in the trial field in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Herbaceous perennial.
*Hardiness.*—USDA Zones 4 to 9.
*Size.*—Grows to about 37 cm wide and 38.5 cm tall to top of inflorescences.
*Form.*—Basal clump, with about 16 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 2 inflorescences per stem.
*Size.*—To 35.5 cm tall to a terminal inflorescence and 7 mm wide at base.
*Internode length.*—2 cm to 6 cm.
*Surface texture.*—Strigose.
*Color.*—Yellow Green 146B.

Leaf (basal):

*Type.*—Simple.
*Shape.*—Ovate to lanceolate.
*Arrangement.*—Basal.

*Blade size.*—Grows to 9 cm long and 4.3 cm wide.
*Margins.*—Shallowly serrate.
*Apex.*—Acuminate.
*Base.*—Attenuate, cupped and gathered at base.
*Surface texture.*—Strigose on both sides.
*Venation.*—Pinnate, with 3 main veins, veins Yellow Green 145D on top and bottom.
*Color.*—Topside Green 137A bottom side closest to Yellow Green 147B.
*Petiole description.*—Grows to 10 cm long and 2 mm wide, strigose on top, glabrous on bottom, Yellow Green 146C.

Leaf (stem):
*Type.*—Simple.
*Shape.*—Lanceolate, curl back slightly.
*Arrangement.*—Alternate.
*Blade size.*—Grows to 12 cm long and 4 cm wide.
*Margins.*—Shallowly serrate to entire, slightly undulate.
*Apex.*—Acuminate.
*Base.*—Attenuate.
*Surface texture.*—Strigose on both sides.
*Venation.*—Pinnate, with 3 main veins from the base, veins Yellow Green 145D on top and bottom.
*Color.*—Topside Green 137A bottom side closest to Yellow Green 147B.
*Petiole description.*—On lowermost leaves only, clasping, grows to 6 cm long and 7 mm wide, strigose, Yellow Green 145D in center and topside Green 137A bottom side closest to Yellow Green 147B on leafy sides.

Inflorescence:
*Type.*—Composite on terminal stalked heads.
*Number of flowering stems from the ground.*—About 16.
*Flowering stem.*—Grows to 35.5 cm tall from the base of the plant to the terminal inflorescence and can grow to 13.5 cm long from the top stem leaf to the base of an inflorescence; branched with 1 to 2 inflorescences per stem; diameter growing to 7 mm wide near the inflorescence; strigose; Yellow Green 146B.
*Size.*—Grows to 8.5 cm wide and 4 cm deep as disc enlarges.
*Form.*—Ray florets held mostly horizontally, mature disc is conic.
*Immature inflorescence.*—Grows to 3.8 cm wide and 2.2 cm deep, ray florets held at an angle (about 30 degrees from horizontal) and rolled up so only the back color shows, closest to N155C, disc color Yellow Green 144A in background with prominent bracts Orange N25A.
*Ray florets.*—Without pistil or stamen, to 18 in number, grow to 42 mm long and 13 mm wide, oblanceolate with the tip acute, entire margins, base attenuate, glabrous on both sides; topside Red Purple 65C, bottom side closest to Greyed Purple 186C.
*Disc.*—Flat becoming conic, becoming 25 mm deep and 35 mm wide with maturity, Yellow Green 144A in background with prominent bracts Orange 24A overall.
*Disc florets.*—About 250 in number, each with 1 pistil and 4 stamen, grow to 9 mm long and 1.5 mm wide, each with one persistent, very stiff linear bract (13 mm long with the tip Red 46A, then 3 mm Orange 24A, then 4 mm Yellow Green 144A, then White 155A at base); corollas 4 mm long and 1 mm wide, tubular, 5 lobed, glabrous, Yellow Green 146B; pistil 9 mm long, ovary 4 mm long, White NN155D, style 4 mm long Yellow Green 145B, 2-branched stigma spreading, Greyed Purple 187B; stamen 4 mm long, filaments 2 mm long and Yellow Green 145D, anthers 2 mm long and Brown 200D, pollen Yellow Orange 16A.
*Phyllaries.*—In 4 leafy series, area grows to 31 mm wide and 5 mm deep, lobes lanceolate in shape, reflexed, grow to 7 mm long and 3.5 mm wide, Yellow Green 147B, margins strigose, tip acute, strigose on both sides.
*Receptacle.*—Grows to 12 mm wide and 12 mm deep, White 155B.
*Bloom period.*—July through October in Canby, Oreg.
*Fragrance.*—Floral.
*Lastingness.*—Each inflorescence lasts about two weeks in Canby, Oreg.

Seeds: 3 mm long and 2.5 mm wide, oval, Brown 200C.
*Fertility.*—Good.

Disease and pests: No pests or diseases have been observed on plants grown under commercial conditions in Canby, Oreg. No resistances are known.

I claim:

1. A new and distinct *Echinacea* plant as herein illustrated and described.

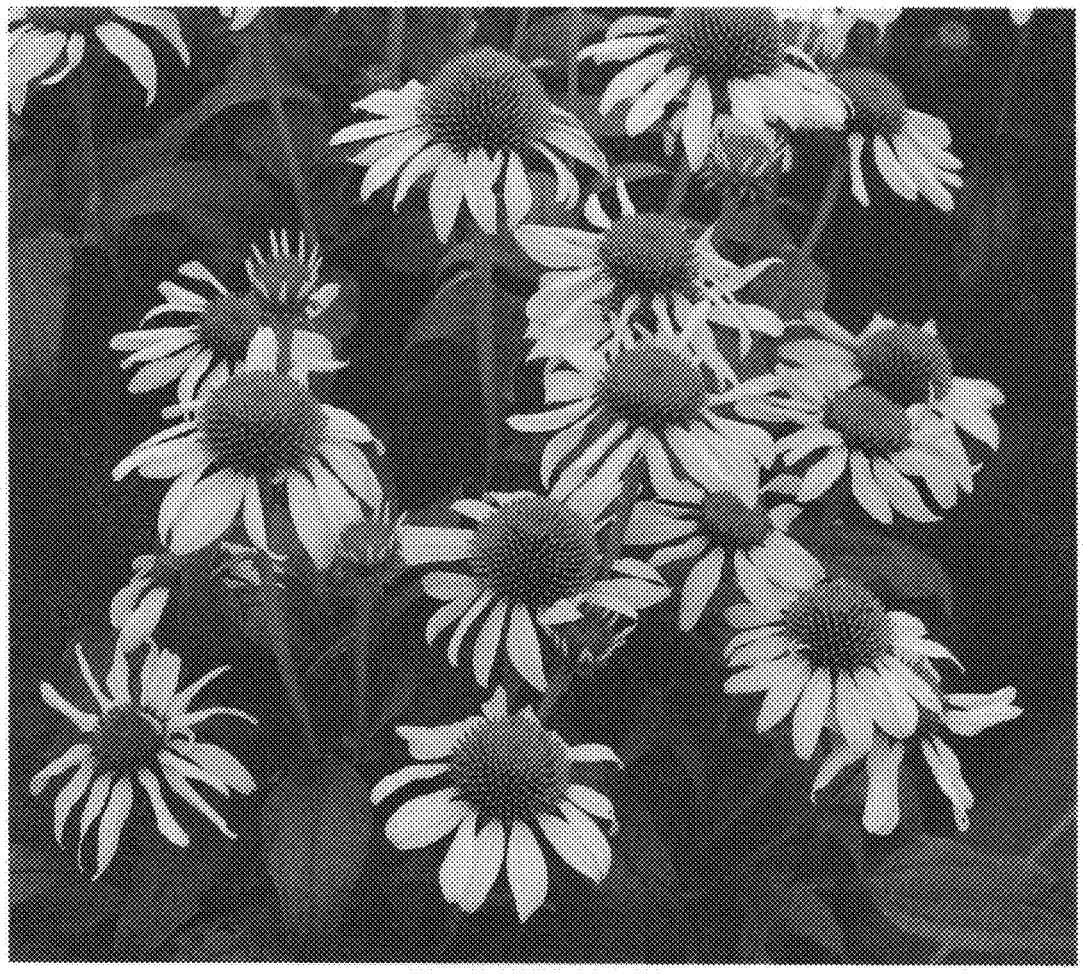

* * * * *